(12) United States Patent
Barone et al.

(10) Patent No.: US 12,076,188 B2
(45) Date of Patent: *Sep. 3, 2024

(54) METHOD OF USING AN IMAGING CATHETER WITH A REINFORCED SECTION

(71) Applicant: Infraredx, Inc., Burlington, MA (US)

(72) Inventors: David Barone, Lexington, MA (US); Kathleen DeRosa, Manchester, NH (US); Sean P. Madden, Arlington, MA (US); John N. Beck, Hopkinton, MA (US)

(73) Assignee: INFRAREDX, INC., Burlington, MA (US)

( * ) Notice: Subject to any disclaimer, the term of this patent is extended or adjusted under 35 U.S.C. 154(b) by 197 days.

This patent is subject to a terminal disclaimer.

(21) Appl. No.: 17/724,891

(22) Filed: Apr. 20, 2022

(65) Prior Publication Data

US 2022/0249057 A1 Aug. 11, 2022

Related U.S. Application Data

(63) Continuation of application No. 16/131,183, filed on Sep. 14, 2018, now Pat. No. 11,331,074.

(Continued)

(51) Int. Cl.
*A61B 8/00* (2006.01)
*A61B 1/01* (2006.01)
(Continued)

(52) U.S. Cl.
CPC ............... *A61B 8/445* (2013.01); *A61B 1/01* (2013.01); *A61B 5/0075* (2013.01);
(Continued)

(58) Field of Classification Search
CPC ... A61B 8/445; A61B 5/02007; A61B 5/0084; A61B 5/6852; A61B 5/0075; A61B 1/01;
(Continued)

(56) References Cited

U.S. PATENT DOCUMENTS

| | | |
|---|---|---|
| 5,024,234 A | 6/1991 | Leary et al. |
| 5,201,316 A | 4/1993 | Pomeranz et al. |

(Continued)

FOREIGN PATENT DOCUMENTS

| | | |
|---|---|---|
| EP | 2478927 A1 | 7/2012 |
| JP | H08206114 A | 8/1996 |

(Continued)

OTHER PUBLICATIONS

Office Action received in European Application No. 18855537.9, dated Oct. 10, 2023 (4 pages).

(Continued)

*Primary Examiner* — Joel Lamprecht
(74) *Attorney, Agent, or Firm* — Jason M. Shapiro; Devlin Law Firm LLC (57) ABSTRACT

A method of imaging a vessel with a catheter includes positioning an imaging tip in a reinforced terminal section of an outer sheath of the catheter, inserting the catheter into a vessel, and performing near infrared spectroscopy of the vessel by retracting the imaging tip to a retracted position proximally spaced from the reinforced terminal section of the outer sheath, transmitting near infrared light from the imaging tip to the vessel wall via the outer sheath, and collecting near infrared light from the vessel wall at the imaging tip via the outer sheath. Transmitting and collecting may be performed after retracting the cable and while the imaging tip is rotated and translated proximally from the retracted position along the outer sheath. Ultrasound energy (Continued)

may be transmitted to the vessel from a transducer on the imaging tip and received from the vessel at the transducer.

10 Claims, 5 Drawing Sheets

Related U.S. Application Data (60) Provisional application No. 62/558,913, filed on Sep. 15, 2017.

(51) Int. Cl.
*A61B 5/00* (2006.01)
*A61B 5/02* (2006.01)
*A61B 8/12* (2006.01)
*A61B 8/08* (2006.01)
*A61M 25/06* (2006.01)
*A61M 25/09* (2006.01)

(52) U.S. Cl.
CPC .......... *A61B 5/0084* (2013.01); *A61B 5/0086* (2013.01); *A61B 5/02007* (2013.01); *A61B 5/6852* (2013.01); *A61B 8/12* (2013.01); *A61B 8/0891* (2013.01); *A61B 2560/0223* (2013.01); *A61M 25/0662* (2013.01); *A61M 25/09* (2013.01)

(58) Field of Classification Search
CPC ....... A61B 5/0086; A61B 8/12; A61B 8/0891; A61B 2560/0223; A61M 25/0662; A61M 25/09
See application file for complete search history.

(56) References Cited

U.S. PATENT DOCUMENTS

| | | | |
|---|---|---|---|
| 5,300,048 A | 4/1994 | Drews, Jr. | |
| 5,443,457 A | 8/1995 | Ginn et al. | |
| 5,445,155 A | 8/1995 | Sieben | |
| 5,458,585 A | 10/1995 | Salmon et al. | |
| 5,546,948 A | 8/1996 | Hamm et al. | |
| 5,715,825 A | 2/1998 | Crowley | |
| 5,738,100 A | 4/1998 | Yagami et al. | |
| 5,976,093 A | 11/1999 | Jang | |
| 6,364,841 B1 | 4/2002 | White et al. | |
| 6,508,804 B2 | 1/2003 | Sarge et al. | |
| 6,615,062 B2 | 9/2003 | Ryan et al. | |
| 6,796,945 B2 | 9/2004 | Belef et al. | |
| 6,949,072 B2 | 9/2005 | Furnish | |
| 7,155,272 B2 | 12/2006 | Yamaguchi et al. | |
| 7,335,180 B2 | 2/2008 | Nita et al. | |
| 7,672,713 B2 | 3/2010 | Furnish | |
| 8,052,605 B2 | 11/2011 | Muller et al. | |
| 8,277,381 B2 | 10/2012 | Zelenka et al. | |
| 8,613,751 B2 | 12/2013 | Nita et al. | |
| 8,814,799 B2 | 8/2014 | Zelenka et al. | |
| 8,864,675 B2 | 10/2014 | Dietz et al. | |
| 8,876,722 B2 | 11/2014 | Waters et al. | |
| 11,331,074 B2 * | 5/2022 | Barone .................... | A61B 1/01 |
| 2002/0026129 A1 | 2/2002 | White et al. | |
| 2004/0106866 A1 | 6/2004 | Ookubo et al. | |
| 2007/0135887 A1 | 6/2007 | Maschke | |
| 2008/0045842 A1 | 2/2008 | Furnish | |
| 2009/0018393 A1 | 1/2009 | Dick et al. | |
| 2009/0088631 A1 | 4/2009 | Dietz et al. | |
| 2009/0163818 A1 | 6/2009 | Zelenka et al. | |
| 2009/0253989 A1 | 10/2009 | Caplan | |
| 2009/0270815 A1 | 10/2009 | Stamp et al. | |
| 2012/0116214 A1 | 5/2012 | Muller et al. | |
| 2012/0165680 A1 | 6/2012 | Akifumi | |
| 2012/0316433 A1 | 12/2012 | Maruyama | |
| 2013/0023771 A1 | 1/2013 | Zelenka et al. | |
| 2013/0253328 A1 | 9/2013 | Zelenka et al. | |
| 2014/0163421 A1 | 6/2014 | Van Hoven | |
| 2014/0378845 A1 | 12/2014 | Nadkarni | |

FOREIGN PATENT DOCUMENTS

| | | |
|---|---|---|
| JP | H0970403 A | 3/1997 |
| JP | 2002360578 A | 12/2002 |
| JP | 2004275784 A | 10/2004 |
| JP | 2006500970 A | 1/2006 |
| JP | 2007505723 A | 3/2007 |
| JP | 2010207612 A | 9/2010 |
| JP | 2011067262 A | 4/2011 |
| JP | 2011519689 A | 7/2011 |
| JP | 2011177231 A | 9/2011 |
| JP | 2015510835 A | 4/2015 |
| WO | 99/16347 | 4/1999 |
| WO | 00/33741 | 6/2000 |
| WO | 2004093963 A1 | 11/2004 |
| WO | 2009137659 A1 | 11/2009 |
| WO | 2010103718 A1 | 9/2010 |
| WO | 2011114600 A1 | 6/2013 |
| WO | 2017143457 A1 | 8/2017 |

OTHER PUBLICATIONS

Office Action received for European Application No. 18857076.6 dated Sep. 21, 2023 (4 pages).
Notice of Allowance in related U.S. Appl. No. 16/131,183 dated Aug. 11, 2021 (11 pages).
Notice of Allowance and Fees Due in related U.S. Appl. No. 16/131,183, dated Mar. 21, 2022 (22 pages).
Office Action in related U.S. Appl. No. 16/131,183 dated Nov. 19, 2021 (15 pages).
Non-Final Office Action received in related U.S. Appl. No. 16/131,183, dated Feb. 18, 2021 (23 pages).
Non-Final Office Action received in related U.S. Appl. No. 16/131,177, dated Feb. 18, 2021 (9 pages).
Notice of Allowance in related U.S. Appl. No. 16/131,177, dated Jan. 13, 2022 (8 pages).
Notification of Reasons For Refusal received in JP app. No. 2020-504008, dated Jan. 25, 2021 (6 pages).
Supplementary European Search Report received in EP app. No. 18855537.9, dated Jan. 14, 2021 (8 pages).
International Preliminary Report on Patentability received in international app. No. PCT/US2018/050997, dated Mar. 26, 2020 (8 pages).
International Preliminary Report on Patentability received in international app. No. PCT/US2018/051000, dated Mar. 26, 2020 (7 pages).
Notification of Reasons For Refusal received in JP app. No. 2020-503904, dated Jan. 29, 2021 (15 pages).
Non-Final Office Action received in related U.S. Appl. No. 16/131,177, dated Feb. 18, 2021 (24 pages).
Notification of Transmittal of International Search Report and Written Opinion including International Search Report and Written Opinion for PCT/US18/50997, mailed Nov. 19, 2018, 14 pages.
Notification of Reasons for Refusal in Japanese Patent Application No. 2020-504008, issued on Oct. 4, 2021 (12 pages), with English translation.
Notification of Reasons for Refusal in Japanese Patent Application No. 2020-503904, issued on Sep. 9, 2021 (7 pages), with English translation.
Final Office Action in related U.S. Appl. No. 16/131,177, dated Aug. 25, 2021 (14 pages).
Extended European Search Report in European Application No. 18857076.6, dated May 17, 2021 (8 pages).
Notification of Transmittal of International Search Report and Written Opinion including International Search Report and Written Opinion for PCT/US18/51000, mailed Dec. 12, 2018, 8 pages.
Sa De Winter et al., A Novel Retrospective Gating Method for Intracoronary Ultrasound Images based on Image Properties, Erasmus (56) References Cited

OTHER PUBLICATIONS

Medical Centre, Rotterdam, The Netherlands, Computers in Cardiology 2003;30:13-16, IEEE, 4 pages.

* cited by examiner

METHOD OF USING AN IMAGING CATHETER WITH A REINFORCED SECTION

CROSS-REFERENCE TO RELATED APPLICATIONS

This application is a continuation of U.S. Non-Provisional patent application Ser. No. 16/131,183, filed on Sep. 14, 2018, which claims priority to U.S. Provisional Patent Application Ser. No. 62/558,913, filed on Sep. 15, 2017, which are incorporated by reference herein in their entirety.

FIELD OF THE INVENTION

The present invention relates generally to catheters and, more particularly, to intravascular catheters for imaging vessels in the human body.

BACKGROUND

Intravascular ultrasound (IVUS) and near-infrared spectroscopy (NIRS) imaging are widely used in interventional cardiology as catheter-carried diagnostic tools for assessing a vessel, such as an artery, within the human body to determine the need for treatment, to guide intervention, and/or to assess the effectiveness of treatment. Guide wire lumen or "monorail" designs employ a guide wire lumen at the distal end of the catheter. The IVUS and NIRS imaging components may then be disposed, typically in some form of housing, in close axially spaced relation to the guide wire lumen.

A key aspect of most imaging catheter designs is the annular thickness of the catheter sheath at the imaging window, typically located immediately proximal or rearward of the juncture between the terminal end of the sheath and a guidewire lumen, and where the near infrared energy passes into and out of the catheter lumen during operation. More specifically, accurate optimal imaging requires the thinnest possible material forming the catheter sheath so as not to unduly attenuate and/or distort the optical signals passing therethrough. However, when the sheath is subjected to axial (i.e., longitudinal) pushing force as the catheter is advanced through the patient's vasculature, a catheter sheath made of thin material tends to bend or kink, thereby preventing the imaging window from being delivered to the intended target location in an artery or the like. More specifically, once the catheter has been kinked, the performance of the catheter is substantially degraded; higher friction will be encountered at the location of the kink, adversely affecting torque transmission, as well as making it more difficult to advance the catheter over the guidewire.

There have been attempts in the prior art to minimize the unwanted bending by strengthening the guidewire lumen. These attempts have met with somewhat limited success. We have found, however, that the location along the length of monorail type imaging catheters that is primarily subject to kinking is at and immediately distal of the imaging window at the terminal end section of the sheath where the transition from the guidewire lumen section to the thin sheath material tends to cause the sheath to bend in response the axial pushing forces in opposition to friction resulting from contact of the guidewire lumen section with the arterial wall.

SUMMARY OF THE INVENTION

In order to minimize the kinking problem described above, the tubing of an imaging catheter, along a terminal length section of the catheter sheath at the imaging window and forwardly thereof to the monorail section, is strengthened against transverse bending or kinking by any of several suitable means. For example, the annular thickness of the near infrared-transparent material at the catheter terminal length section and distally therefrom to the monorail section may be increased sufficiently to resist or prevent kinking. Alternatively, a sleeve of different and more rigid material may be placed about the catheter along the catheter sheath terminal length section. As a still further alternative the sheath terminal length section may be reinforced with embedded material strengthening material or elements. In any of these approaches, the strengthening at the applied location must be sufficient to resist catheter bending or kinking when normal pushing forces are applied longitudinally and resisted by typically occurring opposing forces, such as friction. In addition, the strengthening material may be transmissive to ultrasound energy so that the IVUS components can function properly at the reinforced location.

Although it would be desirable for the employed sheath reinforcement to permit near infrared light to be transmitted therethrough without significant attenuation or distortion, that may not be possible for many, if not most, approaches to cost-effective axial strengthening of the imaging window section of the catheter. Accordingly, in another aspect of the invention, means may be provided for selectively retracting the NIRS light transmitting and receiving components to a section of the catheter located proximally of the reinforced section to an infra-red transparent section of the catheter. Specifically, the optical components located in the catheter lumen for transmitting and receiving near infrared light through the catheter tubing wall can be selectively translated axially to a location where optical transmission through the catheter material is more efficient. Since the IVUS components are typically disposed in fixed spatial relation with the NIRS components (i.e., located in a common housing or other structure), the IVUS components are likewise axially translated.

An imaging catheter according to an example embodiment may comprise an elongate outer sheath made of a material that is transmissive of near infrared light. The outer sheath may include a terminal section at a distal end of the outer sheath and a main section extending from a proximal end of the outer sheath to the terminal section. A guidewire section may extend distally from the distal end of the outer sheath and includes a lumen configured to receive a guidewire. A torque cable may be rotatably disposed in the outer sheath, and an imaging tip may be located at a distal end of the torque cable. The imaging tip may include optical components configured to transmit and receive near infrared light via the outer sheath. The torque cable may be configured to position the imaging tip at the terminal length section of said sheath, and a sheath reinforcement may be disposed along only the terminal section of the outer sheath and may be configured to resist transverse bending of the terminal section of the outer sheath. By reinforcing only the terminal section of the outer sheath, bending and kinking of the outer sheath may be addressed without adversely affecting imaging of the vessel through the main section of the outer sheath.

In an embodiment, the sheath reinforcement includes a sleeve of material annularly abutting and surrounding the terminal length section of the outer sheath. Using a sleeve as a sheath reinforcement can facilitate reinforcement of a conventional outer sheath.

In an embodiment, the sleeve is of the same material as the outer sheath. Forming the sleeve of the same material as the outer sheath may facilitate certain types of imaging through the terminal section of the outer sheath.

In an embodiment, the sleeve is of a material different from that of the outer sheath. Forming the sleeve of a material that is different than that of the outer sheath may allow a thinner sleeve to be used and/or may provide additional or different functionality (such as for calibration purposes).

In an embodiment, the sheath reinforcement is configured to cause the terminal section of the outer sheath to have a flexure modulus more than twice that of the main section of the outer sheath, and preferably more than two and a half times that of the main section of the outer sheath. In an example embodiment, the flexure modulus of the reinforced terminal section of the outer sheath is greater than 160 Mpa. Configuring the sheath reinforcement to impart such values has been found to provide adequate resistance to bending when the catheter is advanced into a vessel.

In an embodiment, a thickness of the terminal section of the outer sheath is more than twice that of the main section of the outer sheath. Configuring the sheath reinforcement to have a thickness more than twice that of the main section of the outer sheath has been found to provide adequate resistance to bending when the catheter is advanced into a vessel.

In an embodiment, the sheath reinforcement has a length that is longer than the imaging tip. Configuring the sheath reinforcement to have a length that is longer than the imaging tip may allow the imaging tip to be better protected as the catheter is advanced into a vessel.

In an embodiment, the sheath reinforcement extends distally beyond the terminal section of the outer sheath to the guidewire section. Configuring the sheath reinforcement to extend distally beyond the terminal section may further improve bending resistance at the terminal section and/or strength of the guidewire section.

In an embodiment, the sheath reinforcement is made of a material that is reflective of near infrared light. In an example embodiment, the sheath reinforcement is doped with material that provides near infrared reflectivity, such as barium sulfate or carbon black. Configuring the sheath reinforcement to be made of a material that is reflective of near infrared light, such as barium sulfate or carbon black, may allow the sheath reinforcement to also be used for calibration purposes.

In an embodiment, the imaging tip further includes an ultrasound transducer and both the terminal section and the sheath reinforcement are both transmissive of ultrasound energy. Providing an ultrasound transducer on the imaging tip and on figuring the sheath reinforcement and terminal section to be transmissive of ultrasound energy may increase usefulness of the catheter by allowing it to be used to obtain ultrasound data in both the terminal and main sections of the outer sheath, even if near infrared data may only be obtained in the main section of the outer sheath.

In an embodiment, the sheath reinforcement has optical characteristics that significantly limit transmission of near infrared light therethrough, and the imaging catheter further comprises a pullback system including a linear translation stage coupled with the torque cable and configured to selectively retract the cable proximally to axially relocate the imaging tip immediately proximal the terminal section of the outer sheath and the sheath reinforcement. Providing a pullback system that includes a linear translation stage coupled with the torque cable and configured to selectively retract the torque cable proximally to relocate or reposition the imaging tip proximally of the terminal section of the outer sheath may facilitate protection of the imaging tip during insertion of the catheter into a vessel and acquisition of data once the catheter is positioned at a desired location in the vessel.

Another aspect of the invention is directed to a method of operating any of the above catheter embodiments comprising, prior to obtaining near infrared spectroscopy data, selectively retracting the torque cable proximally to axially relocate the imaging tip proximal the terminal section of the outer sheath and the sheath reinforcement.

Another aspect of the invention is directed to a method of preventing kinking of a near infrared light transmissive sheath of an intraluminal imaging catheter as the catheter is pushed distally through a blood vessel or the like using a guidewire threaded through a guidewire lumen section at a distal end of the catheter, wherein the sheath includes a terminal section adjacent the guidewire lumen section and a main section extending proximally from the terminal section. The method comprises disposing a sleeve of material in annularly abutting and surrounding relation about only the terminal section of the sheath, and positioning an imaging tip at the distal end of a torque cable in the terminal section of the sheath. In an embodiment, the step of disposing comprises forming the sleeve by molding it with the sheath.

Still another aspect of the invention is directed to a method of imaging a vessel with a catheter including an outer sheath made of a material that is transmissive of near infrared light, a guidewire lumen section extending distally from a distal end of the outer sheath, a cable longitudinally and rotatably disposed lengthwise within the outer sheath, and an imaging tip located at a distal end of the cable and including optical components for transmitting and receiving near infrared light. The method comprises the steps of positioning the imaging tip in a reinforced terminal section of the outer sheath between the guidewire lumen section and an unreinforced main section of the outer sheath, inserting the catheter into a vessel using a guidewire that is threaded through the guidewire lumen section, and performing near infrared spectroscopy of the vessel by retracting the cable to move the imaging tip to a retracted position in the main section of the sheath proximally spaced from the terminal section of the sheath, transmitting near infrared light from the imaging tip to the vessel wall via the outer sheath, and collecting near infrared light from the vessel wall at the imaging tip via the outer sheath. The transmitting and collecting steps are performed after retracting the cable and while the imaging tip is rotated and translated linearly in a proximal direction from the retracted position along the main portion of the outer sheath. Inserting a catheter with an imaging tip located in a reinforced terminal section between the guidewire lumen section and an unreinforced main section helps avoid bending and kinking of the outer sheath, while retracting the imaging tip prior to transmitting and collecting avoids adversely affecting imaging of the vessel through the main section of the outer sheath.

In an embodiment, the method further includes transmitting ultrasound energy to the vessel from a transducer on the imaging tip, and receiving ultrasound energy from the vessel at the transducer, which provides an additional imaging modality that can be employed prior to retracting the cable, after retracting the cable, and/or while the imaging tip is rotated and translated linearly in a proximal direction.

In an embodiment, the imaging tip may be positioned by coupling a proximal end of the cable with a pullback and rotation unit. Using the coupling process to position the imaging tip may provide repeatability.

In an embodiment, the retracting, transmitting, and collecting are automatically performed by a pullback and rotation unit in response to a pullback command, thereby eliminating the possibility of transmitting and collecting near infrared light through the reinforced section by mistake. The pullback command may be received while the catheter is transmitting and receiving ultrasound energy, thereby facilitating multiple imaging modes.

In an embodiment, data acquisition is stopped after receiving a pullback command and resumed after the imaging tip is retracted, thereby avoiding acquisition of data that may be misleading and/or difficult to interpret.

In an embodiment, the reinforced terminal section may be formed of a material that reflects near infrared light, so that the reinforced terminal section may be used to calibrate the imaging tip, thereby eliminating the need for an external calibration target.

BRIEF DESCRIPTION OF THE DRAWINGS

Embodiments of the invention will be described with reference to the following figures, wherein identical structures, elements or parts which appear in more than one figure are labeled with the same reference number, and in which.

DETAILED DESCRIPTION

Figure 1:
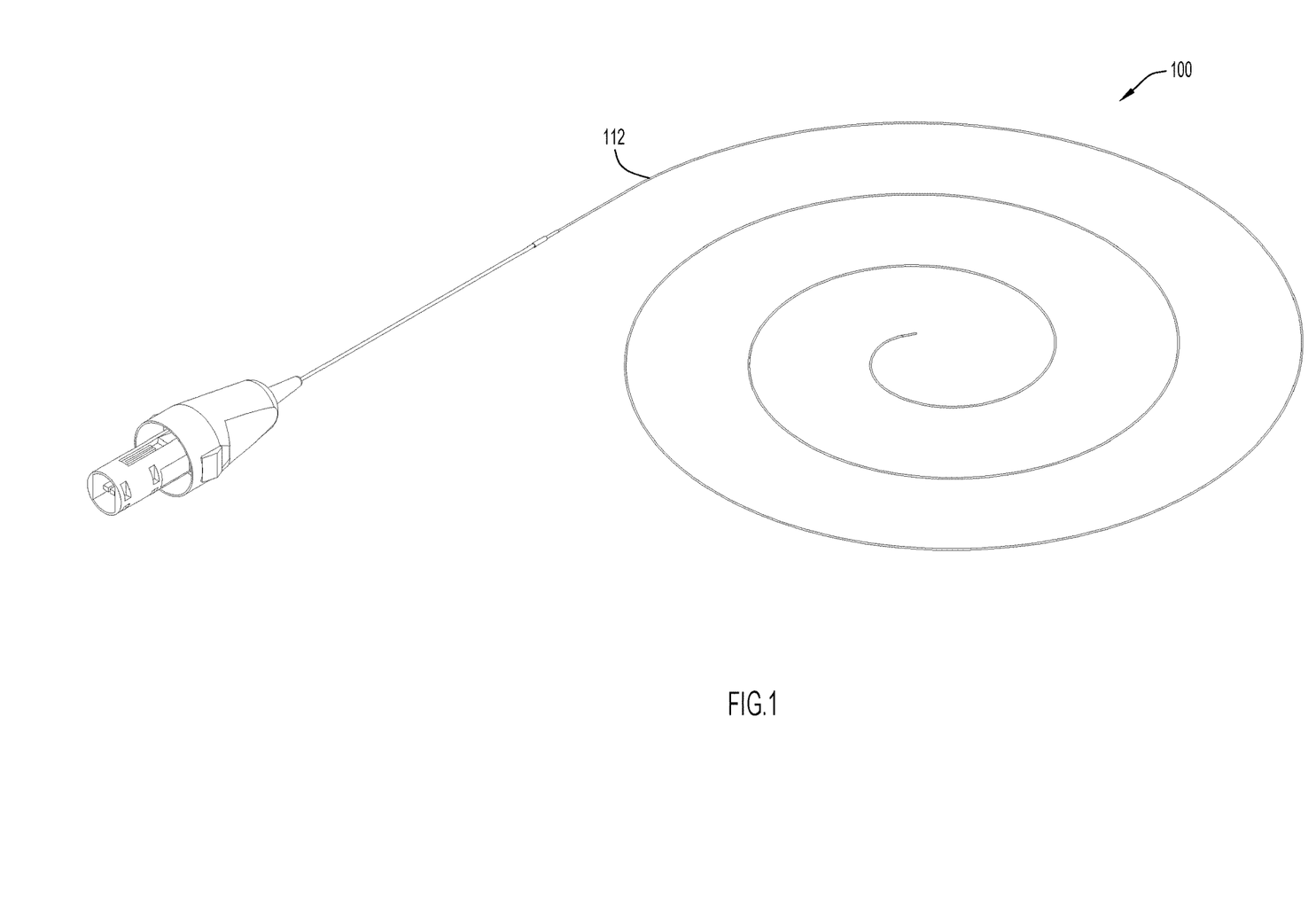
FIG. 1 is a perspective view of an imaging catheter.
Figure 2:
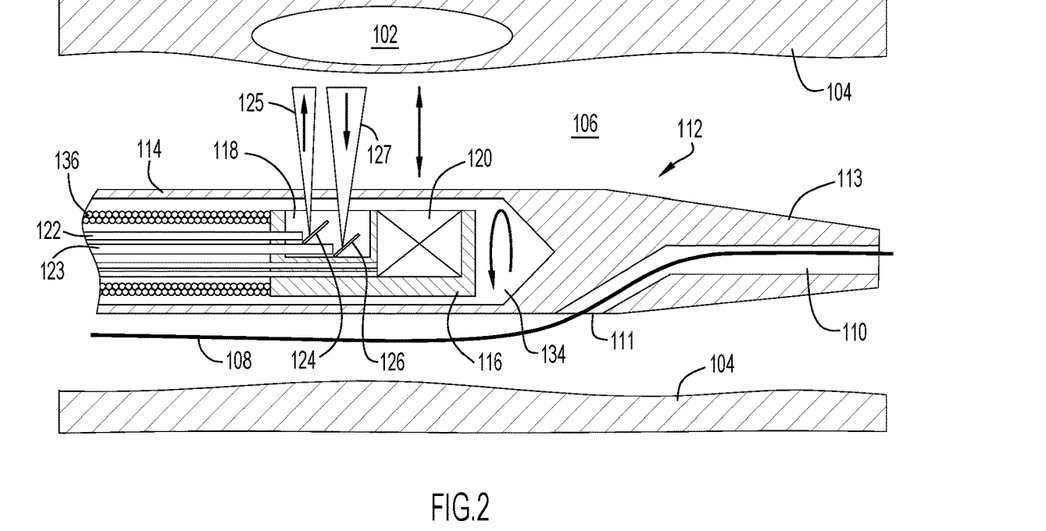
FIG. 2 is a schematic illustration of the imaging window and monorail sections of an imaging catheter according to the prior art showing IVUS and NIRS components located axially to be aligned with the imaging window.

Referring to FIG. 1 and the schematic representation in FIG. 2, an intravascular probe 100 includes an imaging catheter 112 with a guidewire lumen 110 defined in a monorail length section 113 at the distal end of the catheter. The guidewire lumen extends distally from an exit opening 111 defined in the catheter peripheral wall. The catheter comprises a longitudinally extending inner member in the form of a hollow torque cable or tube 136 and an outer sheath layer 114 composed of a material that is efficiently transmissive (i.e., transparent or translucent) to near infrared light. Such material may be, for example, petrothene or any suitable polymer that efficiently transmits infrared light. Inside the sheath 114 there may be a transmission medium 134, such as saline or other fluid, surrounding an ultrasound transducer 120 for providing enhanced improved acoustic transmission for IVUS operation. The transmission medium 134 is also transparent to the infrared light emitted from an optical bench 118 for NIRS operation. The intravascular probe can be inserted into a lumen 106 of an artery using a guidewire 108 that is threaded through the catheter guidewire lumen 110 in monorail section 113.

A delivery optical fiber 122 and a collection optical fiber 123 extend between proximal and distal ends of the catheter 112. The distal ends of both the collection and delivery fibers are secured to optical bench 118. A housing 116 may be located at the distal end or imaging tip of the torque cable 136 and houses and/or provides a mounting support for both the optical bench 118 with its NIRS components and one or more ultrasound transducers 120 serving as the IVUS components. The housing 116, including the optical bench 118 and the ultrasound transducer 120, may also be referred to herein as an imaging tip.

A near infrared light source such as a laser (not shown) couples light into a proximal end of the delivery optical fiber 122 which guides the light distally to the reflective surface of a delivery mirror 124 located on optical bench 118. Mirror 124 is positioned to redirect the delivered light 125 toward the arterial wall 104. A collection mirror 126, also disposed on the optical bench 118, redirects light 127 scattered from various depths of the arterial wall 104 into the distal end of collection fiber 123 which transmits the collected light proximally in the catheter to an optical detector (not shown) for processing and analysis. Other light redirectors can be used in place of mirrors (e.g., prisms, bends in the optical fiber tips, etc.).

The optical detector that receives the collected light from collection fiber 123 produces an electrical signal that contains a spectral signature indicating the composition of the arterial wall 104 and, in particular, whether the composition is consistent with the presence of lipids found in a vulnerable plaque 102. The spectral signature in the electrical signal can be analyzed using a spectrum analyzer (not shown) implemented in hardware, software, or a combination thereof.

At the imaging window section of catheter 112, namely the terminal length section of sheath 114 surrounding the mirrors 124, 126 and ultrasound transducer 120 and extending to the proximal end of monorail section 113, the thin annular wall of sheath 114 optimizes transmission of near infrared light therethrough without significant attenuation and distortion. As described above, it has been found that the thin sheath wall at the imaging window section is particularly subject to kinking or bending when the catheter is pushed through an artery or similar lumen. In accordance with one aspect of the present invention, in order to prevent or minimize the possibility of such kinking, the terminal length section is reinforced or strengthened. In the embodiment illustrated in FIG. 3, this strengthening may be achieved by a sheath reinforcement in the form of a sleeve 140 disposed to annularly abut and surround the sheath terminal length section to be protected. In this case the sleeve extends axially from, or slightly proximally of, the proximal end of the NIRS and IVUS imaging components (i.e., housing 116) to approximately the proximal end of monorail section 113. Thusly positioned the sleeve 140 surrounds and structurally protects the terminal length section of the catheter most susceptible to kinking when the catheter is pushed distally in an artery. Sleeve 140 may be made of a material different from that of the material of catheter sheath 114, or it may be molded from the same material as an annularly thicker integral section of the catheter.

Figure 3:
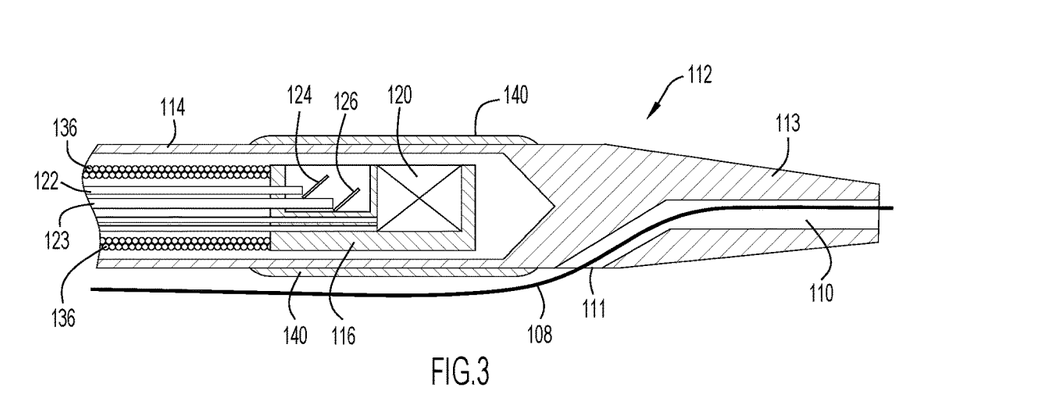
FIG. 3 is a schematic illustration of the imaging window and monorail sections of the imaging catheter of FIG. 2 strengthened against transverse bending according to an embodiment of the invention.
Figure 4:
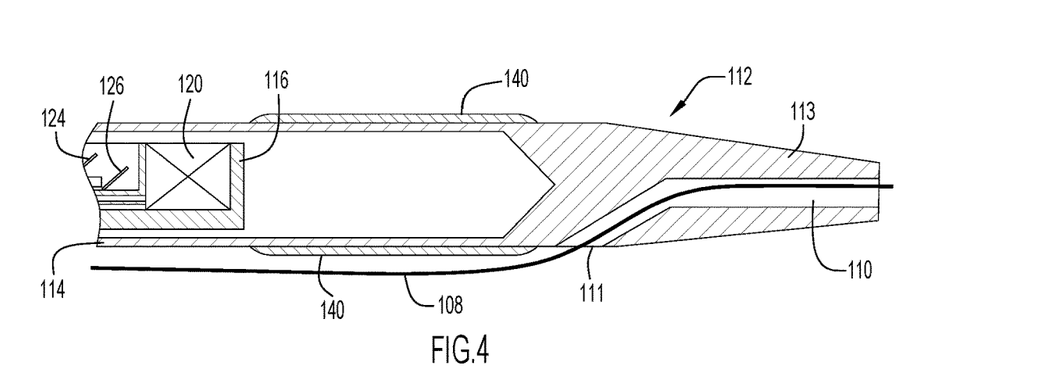
FIG. 4 is a schematic illustration of the imaging window and monorail sections of the imaging catheter of FIG. 3 showing the IVUS and NIRS components retracted proximally of the strengthened section of the catheter.

If sleeve 140 or other sheath reinforcement is constituted such that its presence does not significantly adversely affect transmission (i.e., by distortion and/or attenuation) of near infrared energy through the catheter sheath wall at the imaging window, NIRS and IVUS components can remain in the position shown and function as required. Under any circumstances, the sleeve or its equivalent sheath reinforcement should not adversely affect transmission of ultrasonic energy to and from ultrasound transducers 120 through the catheter sheath. However, cost or other considerations may force the use of sheath reinforcements that attenuate and/or distort near infrared transmission therethrough and thereby preclude effective NIRS operation at the strengthened location. Under such circumstances the imaging components may be selectively pulled a short distance proximally so as to transversely align with a non-reinforced section of the catheter where the annular sheath wall is maximally transmissive to near infrared light. Such a configuration is illustrated in FIG. 4 where the NIRS and IVUS components are shown in a retracted location, having been pulled back by torque cable 136 (FIG. 3) from the terminal length section of the sheath, so as not to be surrounded by sleeve 140. The pullback operation is described in greater detail below.

The material chosen for strengthening the sheath terminal length section may be chosen to permit near infrared reflection measurements to be made for system normalization or calibration purposes. More specifically, if the sleeve 140 is made more highly reflective of near infrared light, with the imaging tip at the distal end of the torque cable positioned in longitudinal alignment with the sleeve, NIRS imaging may be activated. The delivered light, rather than being transmitted out of the catheter to the arterial tissue, will be substantially reflected back from the sleeve to the collection mirror and transmitted back to the processing system as a reference signal. The resulting data can then be used for system normalization. If the sleeve is made of a plastic material, that material may be doped with material (e.g., barium sulfate, carbon black, etc.) that provides the desired near infrared reflectivity characteristics.

Regarding the degree of additional stiffness that should be provided by sleeve 140, Table I below shows measurements of stiffness for ten specimens of catheters at an imaging window location that has not been strengthened according to the present invention. It is noted that mean bending or flexure modulus for these measurements is 60.732 MPa. Table II shows measurements of stiffness for ten specimens of catheters at an imaging window location that has been strengthened according to the present invention. The mean bending or flexure modulus for these measurements is 166.91 MPa, or 2.7 times that for the non-strengthened catheters.

TABLE I a)

| | Specimen Identification | MODULUS [MPa] | Bend Rate [mm/min] | Load at Flex Yield Maximum Point Calculations [N] | Diameter [mm] |
|---|---|---|---|---|---|
| 1 | 1 | 51.678 | 1.0 | 0.12134 | 1.09220 |
| 2 | 2 | 62.852 | 1.0 | 0.12585 | 1.09220 |
| 3 | 3 | 65.636 | 1.0 | 0.10173 | 1.09220 |
| 4 | 4 | 54.113 | 1.0 | 0.09741 | 1.09220 |
| 5 | 5 | 58.030 | 1.0 | 0.10088 | 1.09220 |
| 6 | 6 | 69.470 | 1.0 | 0.11182 | 1.09220 |
| 7 | 7 | 70.698 | 1.0 | 0.12214 | 1.09220 |
| 8 | 8 | 64.727 | 1.0 | 0.11312 | 1.09220 |
| 9 | 9 | 49.218 | 1.0 | 0.10239 | 1.09220 |
| 10 | 10 | 60.899 | 1.0 | 0.10184 | 1.09220 |
| Mean | | 60.732 | 1.0 | 0.10985 | 1.09220 |
| Standard deviation | | 7.34764 | 0.00000 | 0.01041 | 0.00000 |
| Maximum | | 70.698 | 1.0 | 0.12585 | 1.09220 |
| Minimum | | 49.218 | 1.0 | 0.09741 | 1.09220 |
| Mean + 3 SD | | 82.775 | 1.0 | 0.14107 | 1.09220 |
| Mean − 3 SD | | 38.689 | 1.0 | 0.07863 | 1.09220 |

TABLE II b)

| | Specimen Identification | MODULUS [MPa] | Bend Rate [mm/min] | Load at Flex Yield Maximum Point Calculations [N] | Diameter [mm] |
|---|---|---|---|---|---|
| 1 | 1 | 158.447 | 1.0 | 0.33346 | 1.14000 |
| 2 | 2 | 176.793 | 1.0 | 0.31100 | 1.09220 |
| 3 | 3 | 163.882 | 1.0 | 0.29833 | 1.09220 |
| 4 | 4 | 166.549 | 1.0 | 0.30295 | 1.09220 |
| 5 | 5 | 158.116 | 1.0 | 0.30396 | 1.09220 |
| 6 | 6 | 165.268 | 1.0 | 0.30081 | 1.09220 |
| 7 | 7 | 157.906 | 1.0 | 0.28736 | 1.09220 |
| 8 | 8 | 180.179 | 1.0 | 0.30786 | 1.09220 |
| 9 | 9 | 172.945 | 1.0 | 0.29021 | 1.09220 |
| 10 | 10 | 162.820 | 1.0 | 0.28233 | 1.09220 |
| Mean | | 166.291 | 1.0 | 0.30183 | 1.09698 |

TABLE II-continued b)

| Specimen Identification | MODULUS [MPa] | Bend Rate [mm/min] | Load at Flex Maximum Point Yield Calculations [N] | Diameter [mm] |
|---|---|---|---|---|
| Standard deviation | 7.92374 | 0.00000 | 0.01439 | 0.01512 |
| Maximum | 180.179 | 1.0 | 0.33346 | 1.14000 |
| Minimum | 157.906 | 1.0 | 0.28233 | 1.09220 |
| Mean + 3 SD | 190.062 | 1.0 | 0.34501 | 1.14233 |
| Mean − 3 SD | 142.519 | 1.0 | 0.25865 | 1.05163 |

Figure 5:
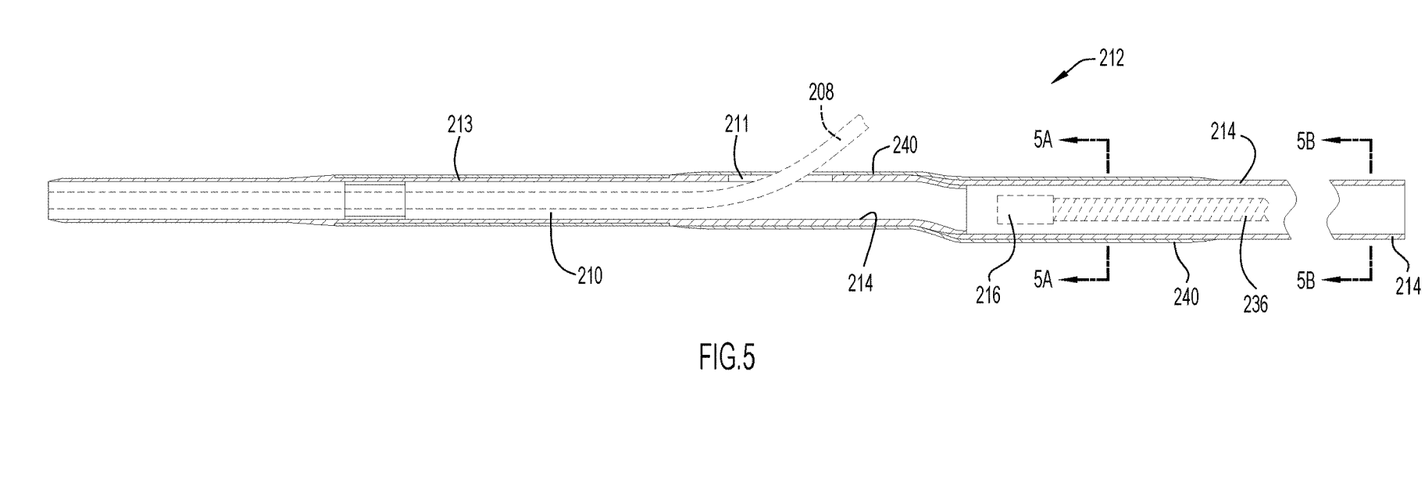
FIG. 5 is a broken cross-sectional side view of an imaging catheter according to an embodiment of the invention.
Figure 5A:
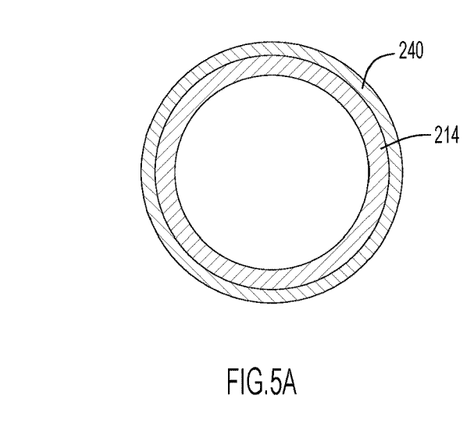
FIG. 5A is a view in transverse cross-section taken along lines 5A—5A in FIG. 5.
Figure 5B:
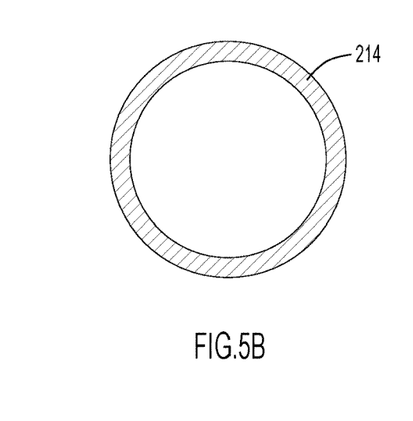
FIG. 5B is a view in transverse cross-section taken along lines 5B—5B in FIG. 5.

A less schematically represented embodiment of a catheter 212 embodying the principles of the invention is illustrated in FIGS. 5, 5A and 5B. The catheter comprises an inner torque cable or tube 236 and an outer infrared transmissive sheath layer 214 composed of a material such as petrothene or any suitable polymer that transmits near infrared light. A guidewire lumen 210 is defined longitudinally through a guidewire or monorail length section 213 extending distally from the terminus of sheath 214 to define the distal end of the catheter. Guidewire lumen 210 extends distally from a guidewire exit opening 211 defined through the catheter peripheral wall. A guidewire 208 may be threaded through the catheter guidewire lumen 210 in monorail section 213 when the catheter is inserted into a lumen of an artery.

Delivery and collection optical fibers (not shown) extend within torque cable 236 between proximal and distal ends of the catheter. A housing 216 may be located at the distal end or tip of the torque cable 236 and houses and/or serves as a mounting support for NIRS components on an optical bench (not shown) and IVUS components in the form of one or more ultrasound transducers (not shown). Operation of the catheter in the IVUS and NIRS modes is as described in connection with FIGS. 2, 3 and 4.

Strengthening of catheter 212 is achieved by means of a sleeve 240 disposed to annularly abut and surround the terminal length section of the catheter to be protected. In this case the sleeve extends axially and distally from a location slightly rearward or proximal of the proximal end of the NIRS and IVUS imaging components (i.e., in housing 216) to slightly beyond the proximal end of monorail section 213. Thusly positioned the sleeve 240 surrounds and structurally protects the terminal length section of the sheath, which is most susceptible to kinking when the catheter is pushed distally in an artery. Sleeve 240 is molded from the same material as the catheter sheath 214, thereby providing the sheath as an annularly thicker integral section of the catheter. Alternatively, the sleeve 240 may be made of a strengthening material different from that of the material of the sheath, such as a plastic, metal, etc., as described above.

In the example shown in FIGS. 5, 5A and 5B, the monorail section 213 has an elongate portion with a longitudinal axis laterally offset from a longitudinal axis of the outer sheath 214, and a small angled portion extending proximally from the elongate portion to the outer sheath. Guidewire exit 211 is formed through the elongate portion of the monorail section 213 distally of the small angled portion. The sleeve 240 extends distally from a location slightly rearward or proximal of housing 216 in its fully extended state, across the small angled portion of the monorail section 213 to a location along the elongate portion of the monorail section distally of the guidewire exit 211. In this way, sleeve 240 may reinforce and strengthen the monorail section 213 in the vicinity of guidewire exit 211 while also resisting bending or kinking of the outer sheath 214 proximally of the monorail section. In the example shown, proximal and distal ends of the sleeve 240 are tapered to avoid edges that can make it more difficult to push the catheter through the vessel and/or damage the vessel wall, and a medial portion of the sleeve is bent at an angle corresponding to the angle of the monorail's angled section. Although these features of the sleeve provide certain advantages, they may also result in non-uniform ultrasound transmissiveness along the length of the sleeve which could potentially be misinterpreted as abnormalities in the vessel.

In the embodiment shown, the reinforced portion of the monorail section 213 in the vicinity of the guidewire exit 211 has a first wall thickness, the reinforced terminal length section of the outer sheath 214 has a second wall thickness smaller than the first wall thickness, and the remainder of the outer sheath 214 has a third wall thickness smaller than the second wall thickness. Thus, it will be appreciated that each of these sections may have a different flexure modulus.

Figure 6:
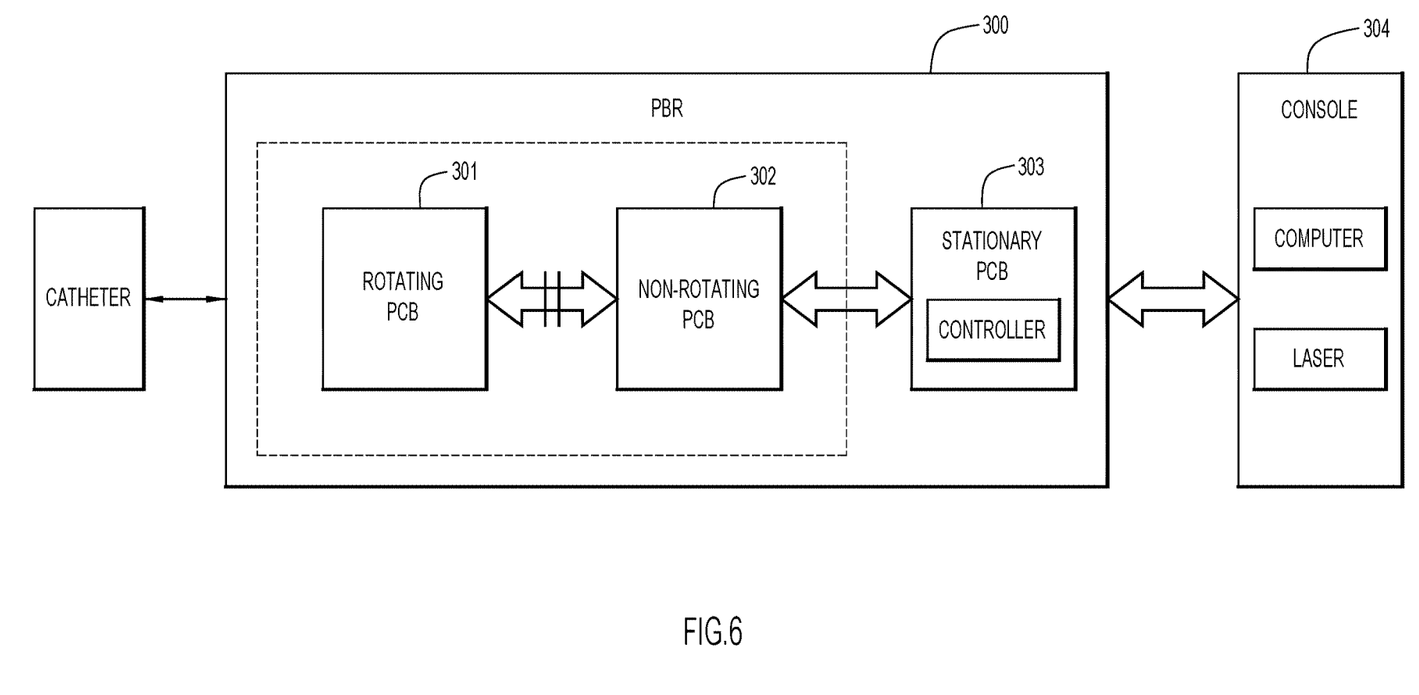
FIG. 6 is a schematic block diagram of pullback and rotation controls for the imaging catheter of FIG. 5.

Exemplary dimensions for the catheter shown in FIGS. 5, 5A and 5B are as follows, it being understood that these dimensions are provided solely as perspective for understanding the invention and are not per se limiting on the scope of the invention:

i. Sleeve 240 axial length: 3.76±0.25 mm
ii. Sleeve 240 outside diameter: 1.118±0.051 mm
iii. Sheath 214 outside diameter: 1.016±0.051 mm
iv. Sheath 214 inside diameter: 0.838±0.001 mm Referring to FIG. 6, which shows how data for pullback and rotation functions are transmitted, a pullback and rotation control unit (PBR) 300 is shown as including a stationary printed circuit board (PCB) controller 303 for controlling a non-rotating PCB section 302 that is linearly movable and a rotating PCB section 301 that rotates and moves linearly. Non-rotating PCB section 302 and rotating PCB section 301 are linearly translatable and signals may be transmitted therebetween via slip rings or the like. Control unit 300 serves to permit controlled rotation and longitudinal translation of the catheter torque cable 136 or 236 in FIGS. 3 and 5, respectively, from an operator console 304 at which a system processor and a near infrared laser are located. Longitudinal translation is effected in a conventional manner, for example by means of a lead screw and rotary motor that power the lead screw via a pulley and belt arrangement. Rotating PCB 301 and the rotary motor may be mounted on a shuttle (indicated by broken lines in FIG. 6) that is movable linearly within PBR 300. Non-rotating PCB section 302 may also be mounted on the shuttle to longitudinally translate with the rotating PCB 301. A motor for effecting linear translation may be mounted on the housing for PBR 300. Motor control, including pullback control, may originate from the stationary PCB controller 303 as shown, or from a controller located on the rotating PCB 301 or the non-rotating PCB 302.

The catheter is shown in a ready position in FIGS. 3 and 5. In the ready position, the imaging tip 116 or 216 is located in the terminal length section of the outer sheath 114 or 214. Preferably, the imaging tip is in its fully distal position in the ready position to provide a reliable reference point for subsequent operations. When a pullback and rotation of the imaging tip is requested from the ready position, the PBR 300 may be configured to inhibit NIRS and IVUS data collection from the imaging tip and linearly retract the imaging tip to a start position proximally spaced relative to the reinforcement means 140 or 240 (i.e., a start position), after which NIRS and/or IVUS data collection may be enabled and the imaging tip may be pulled back and rotated to acquire IVUS and NIRS data along a length of the vessel. Data acquisition between the ready and start positions is preferably inhibited because the sheath reinforcement may be nontransmissive of NIR light and, even if it is transmissive of IVUS energy, the sheath reinforcement may be non-uniform (e.g., uneven, tapered, and/or angled) along its length, which might cause IVUS imaging anomalies that could be mistaken for abnormalities in the vessel.

If the reinforcement means is transmissive of UV energy, the transducer on the imaging tip may be used in the ready position to acquire and display live IVUS (LIVUS) data (e.g., by requesting LIVUS mode on the PBR unit). Alternatively, the imaging tip (and, thus, the transducer) may be retracted from the ready position to a start position proximally spaced relative to the reinforcement means before acquiring and displaying LIVUS data (e.g., by requesting pullback on the PBR). In either case, once in LIVUS mode, the catheter (including the sheath and the imaging tip) may be manually rotated and/or translated as a unit from outside the body to aim the ultrasound transducer within the vessel. Also, controls on the PBR may be used to effect linear translation of the imaging tip (and, thus, the transducer) relative to the outer sheath. In an embodiment, the PBR is configured to rotate the imaging tip as it is retracted or otherwise linearly translated relative to the outer sheath. Rotating the imaging tip during linear translation has been found to improve operation of the catheter in tortuous vessels.

A user may request automatic pullback and rotation of the imaging tip (and, thus, the transducer) while the system is in LIVUS mode. If the system is in LIVUS mode and the imaging tip is in the ready position when automatic pullback and rotation is requested, the PBR may be configured to inhibit data collection and to retract the imaging tip (and, thus, the transducer) relative to the outer sheath, to a position proximally spaced relative to the reinforcement means (e.g., the start position), before initiating the pullback and rotation operation. If the system is in LIVUS mode and the imaging tip is in the start position, or at a location proximally spaced from the start position, the pullback and rotation operation may proceed without an initial retraction of the imaging tip.

Figure 7:
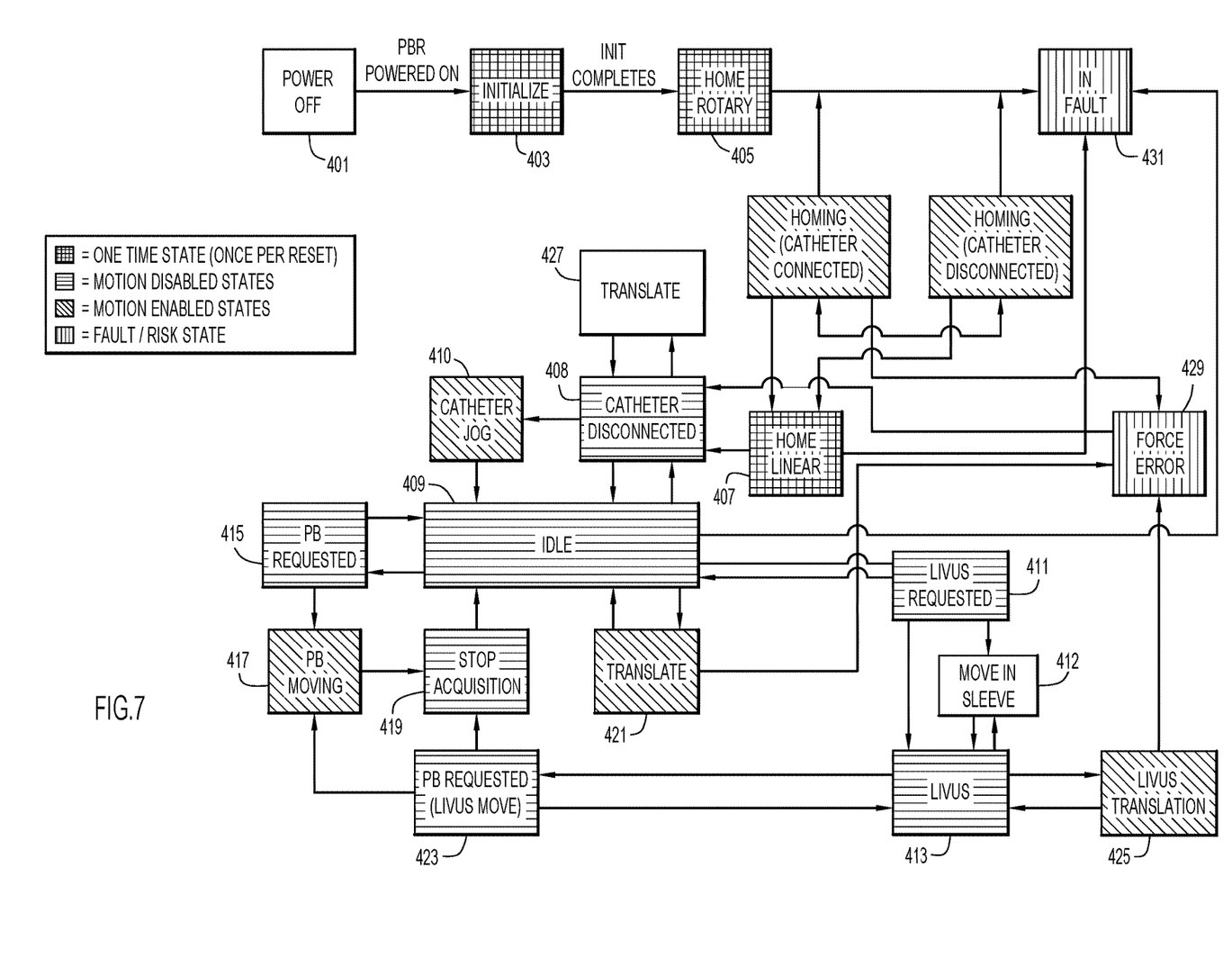
FIG. 7 is a flow chart illustrating the various states of control and operation of the pullback and rotation controls of FIG. 6.

Examples of the various states, modes or conditions of system operation 400 described above are illustrated in the flow chart shown in FIG. 7 to which reference is now made. The system is shown powered off at 401. At power on the system goes through an initialization state or mode 403 and then goes into a home rotary state or mode 405 (e.g., wherein the rotary motor spins the rotary axis of the rotating PCB until it finds an index mark in an encoder). It then places the system in a home linear state or mode 407 (e.g., by moving the lead screw until it finds the boundary of a linear sensor at the desired home position). If the sensor is not found, the user at the console may actuate keys at the console keypad or on the PBR to place the system in the home linear state. When the system is in the home linear state or mode 407 both the rotational and linear axes are at home and the system enters a catheter disconnected state or mode 408 from which it can go to an idle state or mode 409 if a catheter is already connected to the PBR or it can remain in the catheter disconnected mode awaiting connection of a catheter. If a catheter is connected to the PBR in the catheter disconnected mode 408, the system enters a catheter jog state or mode 410 in which the PBR is configured to automatically advance the carriage distally a small distance (e.g., 1 mm) to ensure that the catheter is seated on the nose piece of the PBR. Seating the catheter on the nose piece in this manner ensures proper transfer of linear and rotational forces as well as proper communication of electrical and optical signals across the coupling. In an embodiment, the catheter and PBR may be configured to connect only when the imaging tip is at or very near the ready position (e.g., by configuring hub components of the catheter to align with corresponding portions of the nose piece of the PBR only when the imaging tip is at or very near the ready position). To this end, translation buttons on the PBR may be operable in the catheter disconnected mode 408 to linearly translate the imaging tip to the ready position. If a catheter is then connected, the system moves to the above-described catheter jog state 410, to ensure proper seating of the catheter, and enters the idle mode 409.

Consider the system as being in an idle mode 409 in which the catheter is connected to the PBR and no data is being taken. As noted above, the imaging tip is preferably at or near its ready (e.g., fully distal) position when the system enters the idle mode 409. If LIVUS is requested (e.g., by actuating a LIVUS key on the PBR or console) while the system is in the idle mode 409, the system is placed in the LIVUS requested state or mode 411 and then enters the LIVUS mode 413 in which data is being taken at the imaging tip using the ultrasound transducer. While data being acquired in LIVUS mode 413 may be displayed, the system may or may not be configured to record or save the data while in LIVUS mode. Other possible scenarios include:

1. In Idle mode 409, pullback is requested with the imaging tip in the ready position:
   a. In Idle mode 409, pullback is requested (e.g., by actuating a pullback key on the PBR or console) with the imaging tip in the ready position.
   b. The system enters the LIVUS Requested state or mode 411.
   c. A LIVUS Enable command is generated, and the system enters a Move In Sleeve state or mode 412.
   d. A flag to inhibit data acquisition is set, and data acquisition is inhibited.
   e. Linear axis velocity is obtained from computer storage (e.g., the linear axis velocity may be encoded in executable code) (typically 10 mm/sec).
   f. When the rotary axis speed reaches a predetermined value, linear translation of torque cable begins.
   g. Torque cable is linearly translated to move the imaging tip to a start position that is displaced from its previous position by the axial length of the terminal length section of the outer sheath.
   h. After the imaging tip reaches the start position, the LIVUS mode 413 is entered, and the flag to inhibit data acquisition is cleared.

i. The system resumes sending data from the retracted position.
2. In LIVUS mode 413, pullback is requested with the imaging tip in the ready position:
   a. In LIVUS mode 413, collected data is sent to the computer at the console which may or may not be saving/recording.
   b. Pullback is requested (e.g., by actuating the pullback key or switch on the PBR or console).
   c. Move In Sleeve mode 412 is entered.
   d. A flag to inhibit data acquisition is set, and data acquisition is inhibited.
   e. When rotary axis speed reaches a predetermined speed, linear translation of torque cable begins and imaging tip begins axially traversing reinforcing sleeve.
   f. Torque cable is linearly translated to move imaging tip proximally to a position that is displaced from the ready position by the axial length of the reinforcing sleeve (e.g., the start position).
   g. After the imaging tip reaches the new position, LIVUS mode 413 is entered, and the flag to inhibit data acquisition is cleared.
   h. The system resumes sending IVUS data from the new position.
3. In LIVUS mode, proximal translation is requested with the imaging tip in the ready position.
   a. In LIVUS mode 413, data is sent to the console computer, which may or may not be saving/recording the data.
   b. A command is entered to translate the imaging tip in a proximal direction (e.g., by pressing a key on the PBR unit), placing the system in a LIVUS translation state 425.
   c. A flag to inhibit data acquisition is set and data acquisition is inhibited.
   d. When rotary axis speed reaches a predetermined speed, linear translation of the torque cable begins and the imaging tip begins axially traversing the sheath reinforcement.
   e. The torque cable is linearly translated to move the imaging tip proximally to a position that is displaced from the ready position by the axial length of the sheath reinforcement at the speed selected by the particular translate key. If the user continues to press the translate key after the imaging tip has been repositioned, the imaging tip will continue to be linearly translated at the selected speed. If the user stops pressing the translate key while the imaging tip is being repositioned, the system will continue to move the imaging tip proximally to a position that is displaced from the ready position by the axial length of the sheath reinforcement.
   f. After the imaging tip reaches its new position, LIVUS mode 413 is entered, and the flag to inhibit data acquisition is cleared.
   g. The LIVUS state 413 resumes sending data from its new retracted position.
4. In Idle mode 409, pullback is requested with the imaging tip in the start position:
   a. In Idle mode 409, pullback is requested (e.g., by actuating the pullback key on the PBR or console) with the imaging tip in the start position.
   b. The system enters a Pullback ("PB") Requested state or mode 415 in which the system waits for permission to perform a pullback.
   c. If permission is received within a predetermined time-out period, the system enters a PB Moving state or mode 417 in which the imaging tip is simultaneously rotated and translated proximally and in which data acquisition is enabled. Otherwise, the system returns to the Idle mode 409.
   d. In the PB Moving mode 417, LIVUS and NIR data are collected while the imaging tip is rotated and retracted proximally by the PBR.
   e. If the system senses that the imaging tip has reached the end of its travel, or if the user terminates pullback (e.g., by pressing a stop key on the PBR or the console), the system enters a Stop Acquisition state or mode 419 in which motion and data acquisition are disabled.
   f. The system may then return to the Idle mode 409 (e.g., after a predetermined amount of time or after receiving a command from the console computer), from which the user may enter a Translate state or mode 421 (e.g., by pressing an arrow button on the PBR or console) to return the imaging tip to the start or ready positions.
5. In LIVUS mode 413, pullback is requested with the imaging tip in the start position (e.g., after scenario #2):
   a. In LIVUS mode 413, pullback is requested (e.g., by actuating the pullback key on the PBR or console) with the imaging tip in the start position.
   b. The system enters a Pullback ("PB") Requested state or mode 423 in which the system waits for permission to perform a pullback.
   c. If permission is received within a predetermined time-out period, the rotational speed of the imaging tip is adjusted to a scanning speed and the system enters a PB Moving state or mode 417 in which the imaging tip is simultaneously rotated and translated proximally and in which data acquisition is enabled. Otherwise, the system returns to the LIVUS mode 413.
   d. In the PB Moving mode 417, LIVUS and NIR data are collected while the imaging tip is rotated and retracted proximally by the PBR.
   e. If the system senses that the imaging tip has reached the end of its travel, or if the user terminates pullback (e.g., by pressing a stop key on the PBR or the console), the system enters a Stop Acquisition state or mode 419 in which motion and data acquisition are disabled.
   f. The system may then return to the Idle mode 409 (e.g., after a predetermined amount of time or after receiving a command from the console computer), from which the user may enter a Translate state or mode 421 (e.g., by pressing an arrow button on the PBR or console) to return the imaging tip to the start or ready positions.

In an example embodiment, the initialize state 403, home rotary state 405, and home linear state 407 are examples of one time states (i.e., they occur once per reset). The Idle state 409, LIVUS requested state 411, LIVUS mode 413, PB requested states 415 and 423, and stop acquisition state 417 are examples of linear motion disabled states (i.e., states in which motion of the imaging tip relative to the sheath is disabled) that can occur more than once during a procedure. The PB moving state 417, and the LIVUS translation state 425 are examples of linear motion enabled states (i.e., states in which motion of the imaging tip relative to the sheath is enabled).

In an example embodiment, the PBR 300 may be configured to retract the imaging tip from the ready state at a speed that is different than the speed at which it pulls back the imaging tip from the start state. For example, the PBR may be configured to reposition or retract the imaging tip from the ready state to the start state at 2 mm/sec or 10 mm/sec, and to pull back the imaging tip back from the start state at 0.5 mm/sec, 1 mm/sec, or 2 mm/sec while acquiring data. In an example embodiment, while in LIVUS mode, the imaging tip may be translated by the user at 2 mm/sec or 10 mm/sec.

In an example embodiment, pressure or force sensors may be mounted on the nose piece of the PBR and the system may be configured to monitor an axial force exerted on the nose piece by the inner member (e.g., the torque cable) and to enter a Force Error state or mode 429 when the imaging tip is moving distally in the sheath and the axial force on the nose piece exceeds a predetermined threshold (e.g., suggesting that the rotating imaging tip is encountering a kink in the outer sheath or an extremely tortuous anatomical feature or user error). Since excessive force can indicate a dangerous condition (e.g., a risk of penetration through the outer sheath), in the Force Error mode 429, the system may perform one or more remedial actions. For example, the system may automatically stop rotation and/or further linear translation of the imaging tip. Alternatively, the system may automatically retract the imaging tip proximally a predetermined distance (e.g., 10 mm). The system may continue to rotate the imaging tip during retraction following a force error event.

For any fault other than a force error, the system may be configured to enter an In Fault state or mode 431 in which the system automatically stops rotation and linear translation of the imaging tip.

It will be appreciated that the particular modes and states described above and illustrated in FIG. 7 represent a particular embodiment of a system in which an imaging tip in an imaging catheter may be selectively pulled back or retracted from a position at a specified length section of the catheter. The pullback may be necessitated because of degradation of transmissivity of light (e.g., near infrared light) at the specified length section due to structural enhancement thereof or for other reasons (such as non-uniformity of ultrasound transmissiveness). It will be appreciated that various modifications can be made. For example, when a pullback and rotation is requested from a ready/idle state, the PBR may be configured to inhibit data collection and linearly retract the imaging tip to a position proximally spaced relative to the reinforcement means, after which data collection may be enabled and the imaging tip may be pulled back and rotated to collect NIR and/or IVUS data. It will also be appreciated that, instead of selectively retracting the imaging tip prior to collecting data, data may be collected through the reinforcement means and subjected to data processing specific to the reinforced section which differs from the normal data processing used to process data collected through unreinforced sections of the catheter.

The above-described embodiments are provided by way of example and are not intended to limit the scope of the invention. Persons of ordinary skill in the art will appreciate that various modifications and changes may be made without departing from the spirit and scope of the invention. It should be understood that features described with respect to one embodiment may be used with other embodiments.

The invention claimed is:

1. A method of imaging a vessel with a catheter including an outer sheath made of a material that is transmissive of ultrasound energy, a guidewire lumen section extending distally from a distal end of the outer sheath, a cable longitudinally and rotatably disposed lengthwise within the outer sheath, and an imaging tip located at a distal end of the cable and including an ultrasound transducer, the method comprising the steps of:
   positioning the imaging tip in a reinforced terminal section of the outer sheath between the guidewire lumen section and an unreinforced main section of the outer sheath;
   inserting the catheter into a vessel with the imaging tip positioned in the reinforced terminal section of the outer sheath, wherein the inserting step is performed using a guidewire that is threaded through the guidewire lumen section; and
   performing imaging of the vessel by:
   retracting the cable to move the imaging tip from the reinforced terminal section of the outer sheath to a retracted position in the main section of the outer sheath proximally spaced from the terminal section of the outer sheath;
   transmitting ultrasound energy from the imaging tip to the vessel wall via the outer sheath; and
   receiving ultrasound energy from the vessel wall at the imaging tip via the outer sheath;
   wherein the transmitting and receiving steps are performed after retracting the cable and while the imaging tip is rotated and translated linearly in a proximal direction from the retracted position along the main portion of the outer sheath.

2. The method of claim 1, wherein the steps of transmitting and receiving ultrasound energy are performed via the terminal section of the outer sheath prior to retracting the cable.

3. The method of claim 1, wherein positioning the imaging tip includes coupling a proximal end of the cable with a pullback and rotation unit.

4. The method of claim 3, wherein retracting includes holding the outer sheath stationary and retracting the cable with the pullback and rotation unit.

5. The method of claim 3, wherein the imaging tip is rotated and translated linearly in a proximal direction using the pullback and rotation unit.

6. The method of claim 3, further comprising receiving a pullback command at the pullback unit, and wherein the steps of retracting, transmitting, and receiving are automatically performed by the pullback and rotation unit in response to the pullback command.

7. The method of claim 6, wherein the pullback command is received while the cathether is transmitting and receiving ultrasound energy.

8. The method of claim 6, further comprising performing data acquisition, wherein data acquisition is stopped after receiving the pullback command and is resumed after the imaging tip is retracted.

9. The method of claim 2, wherein the retracting step is performed after the steps of transmitting and receiving ultrasound energy at the terminal section of the outer sheath.

10. The method of claim 2, further comprising stopping transmission and reception of ultrasound energy at the terminal section of the outer sheath prior to the retracting step and resuming transmission and reception of ultrasound energy after the retracting step.

* * * * *